(12) United States Patent
Glinka et al.

(10) Patent No.: US 7,109,190 B2
(45) Date of Patent: Sep. 19, 2006

(54) CARBACEPHEM β-LACTAM ANTIBIOTICS

(75) Inventors: Tomasz W. Glinka, Cupertino, CA (US); Scott J. Hecker, Del Mar, CA (US)

(73) Assignee: Trine Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 10/833,599

(22) Filed: Apr. 27, 2004

(65) Prior Publication Data

US 2005/0004095 A1  Jan. 6, 2005

Related U.S. Application Data

(60) Provisional application No. 60/466,982, filed on Apr. 30, 2003.

(51) Int. Cl.
 C07D 463/22 (2006.01)
 A61K 31/4353 (2006.01)
 A61P 31/04 (2006.01)

(52) U.S. Cl. .................. 514/210.04; 540/205
(58) Field of Classification Search ................ 540/205; 514/210, 210.04
 See application file for complete search history.

(56) References Cited

U.S. PATENT DOCUMENTS

| | | | | |
|---|---|---|---|---|
| 4,640,919 A | * | 2/1987 | Mochida et al. ............. | 514/241 |
| 4,788,185 A | * | 11/1988 | Miyake et al. ............... | 514/205 |
| 4,826,834 A | * | 5/1989 | Yoshimura et al. .......... | 514/207 |
| 5,077,287 A | * | 12/1991 | Ternansky ............. | 514/210.04 |
| 5,565,445 A | * | 10/1996 | Cama et al. ............ | 514/210.04 |

OTHER PUBLICATIONS

Robert J. Ternansky, J. Med Chem 36 pp. 1971-1976 (1993).*
* cited by examiner

*Primary Examiner*—Mark L. Berch
(74) *Attorney, Agent, or Firm*—Squire, Sanders & Dempsey L.L.P.

(57) ABSTRACT

The present invention relates to carbocephem β-lactam antibiotics having the chemical structure:

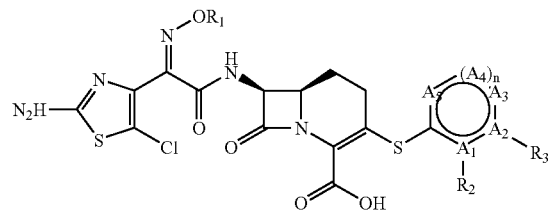

wherein the compounds are useful for the treatment of bacterial infections, in particular those caused by methicillin-resistant *Staphylococcus* spp.

12 Claims, No Drawings

CARBACEPHEM β-LACTAM ANTIBIOTICS

RELATED APPLICATIONS

This application is based on and claims the benefit of Provisional Patent Application Ser. No. 60/466,982, filed 30 Apr. 2003, which is incorporated by reference as if fully set forth herein.

FIELD OF THE INVENTION

The present invention relates to organic chemistry, medicinal chemistry, biochemistry, biology and medicine. In particular, it relates to carbacephem β-lactam antibiotics, pharmaceutically acceptable salts thereof and the use of either the compound or its salt to treat bacterial infections, especially infections caused by bacterial species resistant to conventional β-lactams.

BACKGROUND OF THE INVENTION

The following is provided as background information only and is not to be construed as prior art to the present invention.

Over the past three decades a variety of antibiotics have become available for clinical use. One class of antibiotics that has seen remarkable growth is the β-lactams, over 70 of which have entered clinical use since 1965. Unfortunately, the widespread use of these antibiotics has resulted in an alarming increase in the number of resistant strains, especially among clinically important bacteria such as the genera *Salmonella*, *Enterobacteriaceæ*, *Pseudomonas* and *Staphylococcus*.

Bacterial resistance to cephalosporins occurs primarily through three mechanisms: (a) destruction of the antibiotic by β-lactamases; (b) decreased penetration due to changes in bacterial outer membrane composition; and (c) alteration of penicillin-binding proteins (PBPs) resulting in interference with β-lactam binding. The latter pathway is especially important, as the binding of β-lactams to PBPs is essential for inhibiting peptidoglycan biosynthesis (peptidoglycan is a required bacterial cell-wall component). Certain gram-positive bacteria such as methicillin-resistant *Staphylococcus aureus* ("MRSA") and various genus *Enterococcus* bacteria are highly resistant to beta-lactam antibiotics. The resistance of MRSA is due to the presence of a PBP called PBP2a, which binds very poorly to β-lactam antibiotics. The options for treating infection caused by MRSA are limited and there is a need for new antibiotics with activity against these strains.

In recent years, a novel family of β-lactam antibiotics, the carbacephems (1), has been sporadically touted as having promise against MRSAs and other resistant species. In compound (1), $R_1$ and $R_2$ are variously described as a wide range of aromatic and heteroaromatic entities. $R_3$ has generally been reported as an optionally substituted alkyl group. For example,

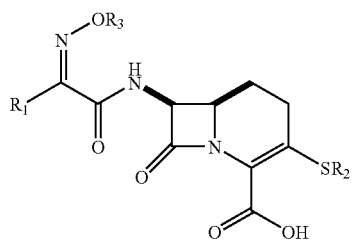

(1)

in Ternansky, et al., *J. Med. Chem.*, 1993, 1971, compounds of general structure (1), in which $R_1$ is 2-amino-4-thiazolyl, $R_3$ is 2-fluoroethyl and $R_2$ is alternately 1,3,4-thiadiazol-2-yl(2), 6-nitrobenzothiazol-2-yl (3) or pyridino[3,4-d]thiazol-2-yl(4), are disclosed.

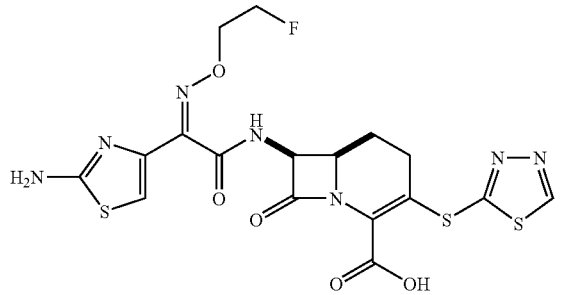

(2)

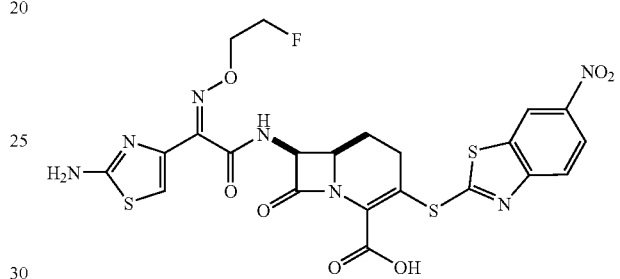

(3)

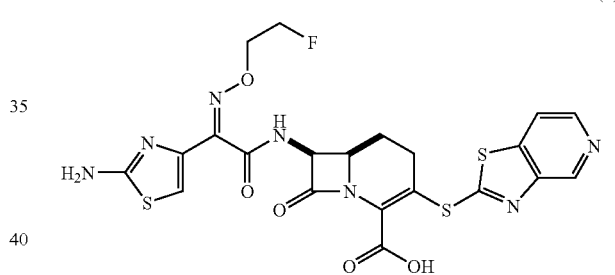

(4)

The problem with the above compounds and, presumably, the carbacephems in general, is that researchers investigating the family have been unable to achieve an acceptable balance between MRSA potency and serum protein binding. That is, MRSA activity was demonstrated relatively early on to correlate with lipophilicity; the more lipophilic the carbacephem, the greater its potency. Unfortunately, the greater the lipophilicity of the compound, the greater is its tendency toward high protein binding. Such binding is undesirable because it reduces the compound's bioavailability. In compounds (2), (3) and (4), for example, the peripheral fluoroethyl group was likely used in an attempt to circumvent the problem by affording some lipophilicity to the compound as a whole while maintaining a lower level of lipophilicity in the core molecule. The effort appears to have been unsuccessful since compound (2) exhibited a good MIC (2 μg/mL) but poor serum binding (>99.2%), compound (3) exhibited a fair MIC (4 μg/mL) but also showed poor serum binding (99.6%) and compound (4) exhibited excellent low, 36%, serum binding but an extremely poor MIC (64 μg/mL).

Despite the above, the carbacephems remain an intriguing approach to dealing with MRSA and other resistant bacterial species. What is needed, however, is a class of carbacephems that achieves the requisite balance of MRSA potency and protein binding. The present invention provides such a class of compounds.

SUMMARY OF THE INVENTION

Thus, in one aspect, the present invention relates to a compound having the chemical formula:

[Chemical structure]

or a salt thereof, wherein:
n is 0 or 1, wherein:
  when n is 0:
    $A_1$ is selected from the group consisting of oxygen and sulfur;
    $R_2$ does not exist;
    $A_2$, $A_3$ and $A_5$ are selected from the group consisting of carbon and nitrogen such that the resulting 5-member ring is aromatic; and, $R_3$ is selected from the group consisting of hydrogen, —$NH_2$, and —$CH_2S(CH_2)_2NH_2$;
  when n is 1:
    $A_1$ is carbon;
    one or two of $A_2$, $A_3$, $A_4$ and $A_5$ is/are nitrogen, the rest are carbon;
    $R_2$ is —$CH_2S(CH_2)_2NH_2$; and,
    if $A_2$ is carbon, $R_3$ is hydrogen; if $A_2$ is nitrogen, $R_3$ does not exist;
$R_1$ is selected from the group consisting of:
  hydrogen;
  —$CH_3$;
  —$CH_2CH_3$;
  —$CH_2F$; and,
  —$CH_2CH_2F$.

In an aspect of this invention, n is 0, $A_1$ is sulfur, two of $A_2$, $A_3$ and $A_5$ are nitrogen, the remaining "A" being carbon, and $R_3$ is hydrogen.

In an aspect of this invention, n is 0, $A_1$ is sulfur, two of $A_2$, $A_3$ an $A_5$ are nitrogen, the remaining "A" being carbon, and $R_3$ is —$NH_2$.

In an aspect of this invention, n is 0, $A_1$ is sulfur, $A_2$ is carbon, $A_3$ and $A_5$ are nitrogen and $R_3$ is hydrogen.

In an aspect of this invention, n is 0, $A_1$ is sulfur, $A_2$ is carbon, $A_3$ and $A_5$ are nitrogen and $R_3$ is —$NH_2$.

An aspect of this invention is a compound having the chemical structure:

[Chemical structure]

An aspect of this invention is a compound having the chemical structure:

[Chemical structure]

In an aspect of this invention, n is 1, and one of $A_2$, $A_3$, $A_4$ and $A_5$ is nitrogen, the others being carbon.

In an aspect of this invention, n is 1, $A_2$ is nitrogen, and the other "A" groups are carbon.

In an aspect of this invention, n is 1, $A_3$ is nitrogen, and the other "A" groups are carbon.

An aspect of this invention is a compound having the chemical structure:

[Chemical structure]

An aspect of this invention is a chemical compound having the chemical structure:

[Chemical structure]

An aspect of this invention is a method of treating or preventing an bacterial infection comprising administering a pharmaceutically effective amount of a compound of this invention or a salt thereof to a patient in need thereof.

In an aspect of this invention, the bacterial infection is caused by a β-lactam antibiotic-resistant bacterium.

In an aspect of this invention, the β-lactam antibiotic-resistant bacterium is a methicillin-resistant genus *Staphylococcus* bacterium.

An aspect of this invention is a pharmaceutical composition comprising a compound or salt hereof and one or more pharmaceutically acceptable excipients.

DETAILED DESCRIPTION OF THE INVENTION

Brief Description of the Tables
  Table 1 shows the MICs and human serum binding values of representative compounds of this invention.

Definitions
  The term "method" refers to manners, means, techniques and procedures for accomplishing a given task including, but not limited to, those manners, means, techniques and procedures either known, or readily developed from those manners, means, techniques and procedures known, to practitioners of the chemical, pharmaceutical, biological, biochemical and medical arts.

A "pharmaceutical composition" refers to a mixture of one or more of the compounds of this invention, or physiologically acceptable salts thereof, with pharmaceutically acceptable excipients. The purpose of a pharmaceutical composition is to facilitate administration of a compound to an organism.

A "pharmaceutically acceptable salt," which, for the purposes of this discussion includes a veterinary or agriculturally acceptable salt, of a compound of this invention refers to the compound in a charged form, either a cation or an anion, along with a counter-ion wherein the counter-ion does not adversely affect the activity of the compound or the well-being of the patient. When the compound of this invention is negatively charged, the positively charged counter-ion may be sodium, potassium, lithium, magnesium, calcium, zinc, aluminum, ammonium or any other pharmaceutically acceptable cation known in the art. When the compound of this invention is positively charged, the negatively-charged counter-ion may be chloride, bromide, iodide, nitrate, phosphate, sulfate, acetate, propionate, butyrate, maleate, fumarate, methanesulfonate, ethanesulfonate, 2-hydroxyethylsulfonate, n-propylsulfonate, iso-propylsulfonate, lactate, malate, citrate or any other pharmaceutically acceptable anion known in the art. Salts are prepared by the reaction of a compound herein with an inorganic or organic acid or base. Useful acids include, without limitation, trifluoroacetic, hydrochloric, sulfuric and methanesulfonic acid. Useful bases include, without limitation, benzathene, chloroprocaine, choline, diethanolamine, ethylenediamine, meglumine, procaine, and the hydroxide, alkoxide, carbonate, bicarbonate, sulfate, bisulfate, amide, alkylamide, or dialkylamide salts of, for example, without limitation, the following metal cations: lithium, sodium, potassium, magnesium, calcium, aluminum, and zinc. Such salts may exist as one or more equivalents of acid or base per equivalent of compound or as one or more equivalents of compound per equivalent of acid or base. The compounds herein may also exist an internal salts, so-called zwitterions, in which a basic group on the molecule takes a proton from an acidic group on the molecule to form the salt. Of course, the compounds of the present invention can be prepared as non-pharmaceutically acceptable salts and such salts are within the scope of this invention as well.

As used herein, a "pharmaceutically acceptable excipient," which for the purpose of this discussion includes a veterinary or an agriculturally acceptable excipient, refers to a carrier, diluent or other inert substance that does not cause significant irritation to a patients and does not abrogate the biological activity and properties of the administered compound but that facilitates the administration of a compound to a patient.

"In vitro" refers to procedures performed in an artificial environment such as, e.g., without limitation, in a test tube or culture medium-containing Petri dish.

"In vivo" refers to procedures performed within a living organism such as, without limitation, a mouse, rat, rabbit, dog or human being.

As used herein, a "bacterial infection" refers to the establishment of a sufficient population of a pathogenic bacteria in a patient to have a deleterious effect on the health and well-being of the patient and/or to give rise to discernable symptoms associated with the particular bacteria.

As used herein, the term "MIC," which stands for minimum inhibitory concentration, refers to that concentration, in µg/mL, of a compound of this invention that inhibits the growth and/or proliferation of a strain of bacteria by at least 80% compared to an untreated control.

As used herein, the terms "treat", "treating" and "treatment" refer to a method of alleviating or abrogating a bacterial infection and/or its attendant symptoms once a patient has contracted an infection.

As used herein, the terms "prevent", "preventing" and "prevention" refer to a method for barring a patient from acquiring a bacterial infection in the first place or from re-acquiring an infection after having been treated for it.

As used herein, "administer", "administering," or "administration" refers to the delivery of a compound of this invention, a salt thereof or of a pharmaceutical composition containing the compound or its salt for the purpose of treating or preventing a bacterial infection.

The term "patient" refers to any living entity capable of being infected by bacteria. Thus, a "patient" may be a plant, tree, fish, shellfish, bird, reptile or mammal. Presently preferred patients include mammals such as, without limitation, dogs, cats, horses, cows, pigs, rabbits, goats and sheep. Most preferably, "patient" refers to a human being.

The term "therapeutically effective amount" as used herein refers to that amount of the compound being administered which will relieve to some extent one or more of the symptoms of an infection. That is, a therapeutically effective amount refers to that amount of a compound of this invention that has the effect of (1) reducing, preferably eliminating, a population of pathogenic bacteria in a patient's body, (2) inhibiting (that is, slowing, preferably stopping) proliferation of bacteria in a patient's body, (3) inhibiting (that is, slowing, preferably stopping) spread of a bacterial infection, and/or, (4) relieving to some extent (preferably, eliminating) one or more symptoms associated with a bacterial infection.

The term "prophylactically effective amount" refers to that amount of a compound of this invention that, when administered subsequent to a therapeutically effective amount of a compound hereof or some other antibiotic, has the effect of (1) maintaining a reduced level of a population of bacteria achieved by the therapeutically effective amount; (2) maintaining the level of inhibition of proliferation of bacteria achieved by the therapeutically effective amount; (3) maintaining the level of inhibition of spread of an infection achieved by the therapeutically effective amount; (4) maintaining the level of relief of one or more symptoms or, or if symptoms were eliminated, maintaining the non-existence of symptoms achieved by administration of a therapeutically effective amount of a compound of this invention or some other antibiotic; or, (5) preventing pathogenic bacteria from infecting a patient particularly susceptible to infection, such as patients suffering from immune system-related disorders (e.g., AIDS) or those who have been purposely treated with immuno-suppressants such as transplant recipients whose immune systems are suppressed to discourage transplant rejection.

The term "β-lactam resistant bacterium" refers to bacterium against which a β-lactam antibiotic has a minimum inhibitory concentration (MIC) greater than 8 µg/mL.

Discussion

The present invention provides compounds, methods and compositions effective to treat bacterial infections, in particular those caused by bacteria which have developed resistance to conventional β-lactam antibiotics.

It is well-established that the effectiveness of β-lactam antibiotics is correlated to the amount of time that the concentration of free (unbound) drug exceeds the MIC. A serum protein binding value of >97% is considered too high for a sufficient free drug concentration to be established in a patient using any practical dosing regime. Furthermore, a compound displaying human serum binding of 70% has ten times the amount of free drug as a compound with 97% serum binding (30% vs 3%). The compounds of this invention display excellent (i.e., relatively low) serum binding coupled with MICs of 2 μg/mL or less against strains of methicillin-resistant Staphyloccus aureus.

Syntheses

The syntheses herein are exemplary only and are not intended, nor should they be construed, to be limiting on the scope of this invention in any manner whatsoever. For example, there are numerous approaches to the synthesis of the compounds herein and all such approaches are within the scope of this invention.

EXAMPLE 1

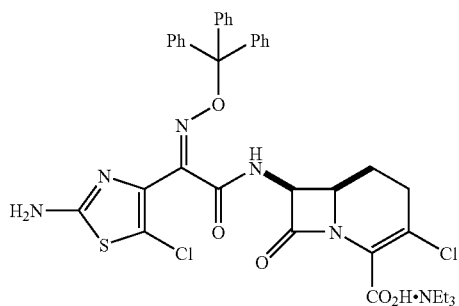

(7R)-7-[(Z)-2-(2-amino-5-chlorothiazol-4-yl)-2-(triphenylmethoxyimino]-acetamido]-3-chloro-8-oxo-1-aza-bicyclo[4.2.0]oct-2-ene-2-carboxylate triethyl amine salt To a solution of bis-(2-benzothiazolyl)-disulfide (4.3 g, 0.013 mol) in dichloromethane (100 mL) was added triphenylphosphine (3.4 g, 0.013 mol). The mixture was stirred for 15 minutes after which (Z)-2-(2-amino-5-chlorothiazol-4-yl)-2-(triphenylmethoxyimino)acetic acid (4.9 g, 0.010 mol) was added. The mixture was stirred for 1 hour and was cooled to 0° C. In a separate flask, (7R)-7-amino-3-chloro-8-oxo-1-aza-bicyclo[4.2.0]oct-2-ene-2-carboxylic acid trifluoroacetic acid salt (2.6 g, 0.008 mol) was suspended in dichloromethane (50 mL) and triethylamine (4.0 g, 0.04 mol) was added. The suspension was stirred for 0.5 hour at room temperature and then was transferred to the flask containing the activated ester of 7-[(Z)-2-(2-amino-5-chlorothiazolyl-4)-2-trityloxyimino] carboxylic acid. The resulting clear solution was allowed to warm to room temperature and was stirred for 48 hours. The reaction mixture was washed twice with 100 mL portions of water, and the organic layer was separated, dried over anhydrous MgSO$_4$, filtered and concentrated to approximately 50 mL. The oily residue was treated with diethyl ether (250 mL), and the solid was filtered and dried giving 6.5 g of crude product. HPLC analysis indicated that it contained approximately 3.0 g. (0.004 mol) of the desired compound as the triethylamine salt.

$^1$H NMR 400 MHz, (DMSO-d$_6$) δ 1.63–1.77 (m, 2H), 2.21–2.41 (m, 2H), 3.77–3.82 (m, 1H), 5.47 (dd, J=9 Hz, J=5 Hz, 1H), 7.11–7.41 (m, 15H), 9.44 (d, J=9 Hz, 1H).

EXAMPLE 2

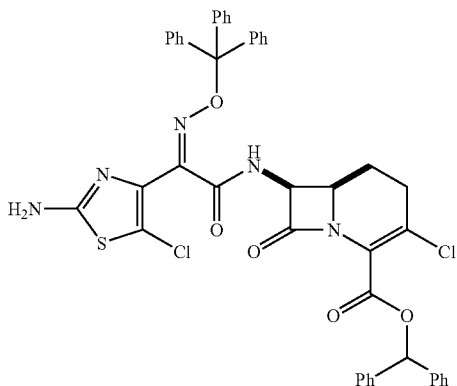

(7R)-7-[(Z)-2-(2-amino-5-chlorothiazol-4-yl)-2-(triphenylmethoxyimino]-acetamido]-3-chloro-8-oxo-1-aza-bicyclo[4.2.0]oct-2-ene-2-carboxylate diphenylmethyl ester The crude (7R)-7-[(Z)-2-(2-amino-5-chlorothiazol-4-yl)-2-triphenylmethoxyimino]-acetamido]-3-chloro-8-oxo-1-aza-bicyclo[4.2.0]oct-2-ene-2-carboxylic acid triethylamine salt (6.5 g.) was dissolved in dichloromethane (200 mL) and was washed twice with 50% H$_3$PO$_4$/H$_2$O and then with water. The organic layer was dried over anhydrous MgSO$_4$, filtered and treated with diphenyldiazomethane solution in dichloromethane (40 mL of 0.5 mol/L solution, 0.02 mol), followed by stirring at room temperature for 1 hour. The reaction mixture was concentrated to dryness and the residue was dissolved in ethyl acetate (20 mL). The ethyl acetate solution was then chromatographed on silica gel (200 g). Nonpolar byproducts were eluted with ethyl acetate:hexane (1:6), and the product with ethyl:acetate:hexane (1:1). After evaporation, the title ester (3.7 g.) was obtained. HPLC indicated that it contained approximately 3.5 g. (0.004 mol) of the desired product.

$^1$H NMR 400 MHz, (DMSO-d$_6$) δ 1.71–1.82 (m, 2H), 2.56–2.66 (m, 2H), 3.96–4.00 (m, 1H), 5.68 (dd, J=9 Hz, J=5 Hz, 1H), 6.94 (s, 1H), 7.28–7.36 (m, 21H), 7.44 (d, J=7 Hz, 2H), 7.54 (d, j=7 Hz, 2H), 9.50 (d, J=9 Hz, 1H).

EXAMPLE 3

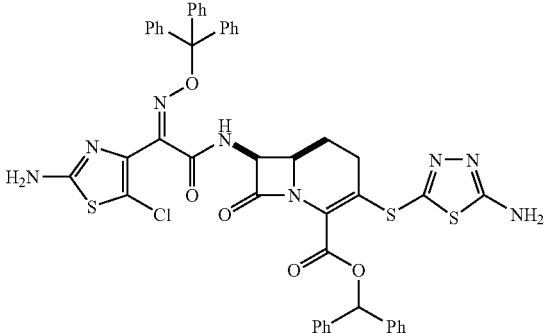

(7R)-7-[(Z)-2-(2-amino-5-chlorothiazol-4-yl)-2-(triphenylmethoxyimino]-acetamido]-3-[5-amino-1,3,4-thiadiazol-2-ylthio]-8-oxo-1-aza-bicyclo[4.2.0]oct-2-ene-2-carboxylate diphenylmethyl ester To a solution of 5-amino-1,3,4-thiadiazole-2-thiol (0.6 g., 0.0045 mol) in dimethylformamide (25 mL) was added potassium carbonate (1.0 g, 0.0076 mol). The mixture was stirred for 1 hour at room temperature after which (7R)-7-[(Z)-2-(2-amino-5-chlorothiazol-4-yl)-2-(triphenylmethoxyimino]acetamido]-3-chloro-8-oxo-1-aza-bicyclo[4.2.0]oct-2-ene-2-carboxylate diphenylmethyl ester (3.2 g., 0.0039 mol) was added. Stirring was continued for 18 hours. The mixture was partitioned between ethyl acetate (50 mL) and water (50 mL). The organic layer was separated, washed with water (30 mL), dried over anhydrous $MgSO_4$ and the solvent was removed with a rotary evaporator. The resultant thick oil was treated with diethyl ether (50 mL) and the solid which formed was filtered and dried to give 2.6 g of crude product.

$^1$H NMR 400 MHz, (DMSO-$d_6$) δ 1.53–1.71 (m, 2H), 2.18–2.21 (m, 2H), 3.88–3.93 (m, 1H), 5.65 (dd, J=9 Hz, J=5 Hz, 1H), 6.90 (s, 1H), 7.20–7.40 (m, 21H), 7.52 (d, J=7 Hz, 2H), 7.68 (d, J=7 Hz, 2H), 7.72 (s, 2H), 9.48 (d, J=9 Hz, 1H).

EXAMPLE 4

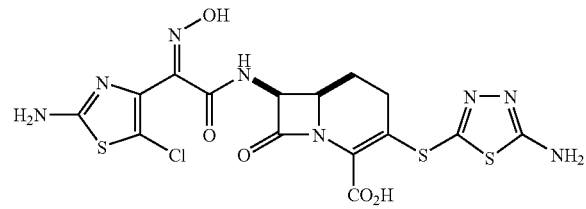

(7R)-7-[(Z) 2-(2-amino-5-chlorothiazol-4-yl)-2-(hydroxyimino]acetamido]-3-[5-amino-1,3,4-thiadiazol-2-ylthio]-8-oxo-1-aza-bicyclo[4.2.0]oct-2-ene-2-carboxylic acid A solution of trifluoroacetic acid (10 mL), triethylsilane (5 mL) and dichloromethane (10 mL) was cooled to 0° C. and (7R)-7-[(Z)-2-(2-amino-5-chlorothiazol-4-yl)-2-(triphenylmethoxyimino]acetamido]-3-[5-amino-1,3,4-thiadiazol-2-ylthio]-8-oxo-1-aza-bicyclo[4.2.0]oct-2-ene-2-carboxylate diphenylmethyl ester from the previous step (2.3 g) was added in portions. The reaction mixture was stirred for 3 hours at 0° C., allowed to warm up to room temperature and evaporated to dryness. The residue was treated with diethyl ether (50 mL) and the solid that formed was filtered and dried to give 2.4 g of crude product. The crude product was purified on HP 20 initially with water elution until the pH was neutral, after which the product was eluted with acetonitrile:water 80:20. The solvent was evaporated to give the 0.65 g of the title compound.

$^1$H NMR 400 MHz, (DMSO-$d_6$) δ 1.53–1.56 (m, 1H), 1.89–1.92 (m, 1H), 2.28–2.34 (m, 2H), 3.80–3.85 (m, 1H), 5.44 (dd, J=9 Hz, J=5 Hz, 1H), 7.28 (s, 2H), 7.63 (s, 2H), 9.12 (d, J=9 Hz, 1H), 11.70 (s, 1H), 13.55 (brs, 1H).

EXAMPLE 5

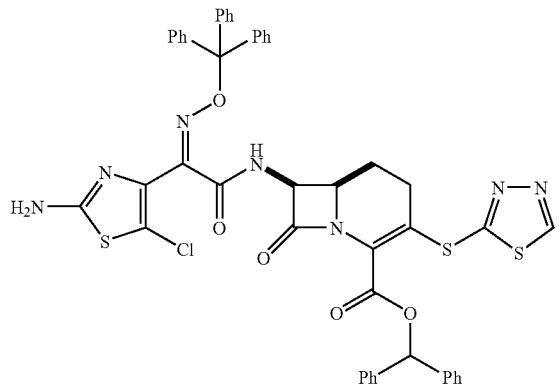

(7R)-7-[(Z) 2-(2-amino-5-chlorothiazol-4-yl)-2-(triphenylmethoxyimino]-acetamido]-3-[1,3,4-thiadiazol-2-ylthio]-8-oxo-1-aza-bicyclo[4.2.0]oct-2-ene-2-carboxylate diphenylmethyl ester To a suspension of 1,3,4-thiadiazole-2-thiol (0.5 g, 0.004 mol) in acetonitile (40 mL) was added sodium hydride (0.2 g, 0.0043 mol) and the mixture was stirred for 1 hour at room temperature. To the resulting suspension was added (7R)-7-[(Z)-2-(2-amino-5-chlorothiazol-4-yl)-2-(triphenylmethoxyimino]-acetamido]-3-chloro-8-oxo-1-aza-bicyclo[4.2.0]oct-2-ene-2-carboxylate diphenylmethyl ester (2.6 g, 0.003 mol), and the mixture was stirred for 48 hours. The solvent was evaporated and the residue was partitioned between water (50 mL) and ethyl acetate (50 mL). The organic layer was dried over anhydrous $MgSO_4$, filtered and evaporated. The resulting solid was treated with diethyl ether (50 mL), and the solid that formed was filtered and dried to give 2.1 g of crude product. The crude product was purified by chromatography on silica gel, eluting with a gradient from ethyl acetate:hexane 1:2 to neat ethyl acetate. The title product was obtained (1.1 g.)

$^1$H NMR 400 MHz, (DMSO-$d_6$) δ 1.66–1.72 (m, 2H), 2.18–2.40 (m, 2H), 3.96–4.02 (m, 1H), 5.71 (dd, J=9 Hz, J=5 Hz, 1H), 6.94 (s, 1H), 7.20–7.40 (m, 21H), 7.45 (d, J=7 Hz, 2H), 7.57 (d, J=7 Hz, 2H), 9.50 (d, J=9 Hz, 1H), 9.73 (s, 1H).

EXAMPLE 6

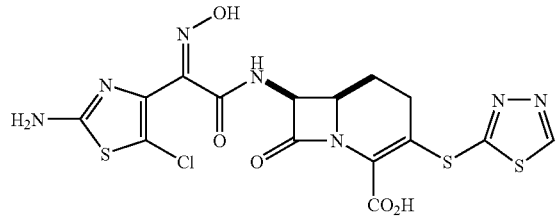

(7R)-7-[(Z) 2-(2-amino-5-chlorothiazol-4-yl)-2-(hydroxyimino]acetamido]-3-[1,3,4-thiadiazol-2-ylthio]-8-oxo-1-aza-bicyclo[4.2.0]oct-2-ene-2-carboxylic acid A solution of trifluoroacetic acid (5 mL), triethylsilane (3 mL) and dichloromethane (8 mL) was cooled to 0° C. and (7R)-7-[(Z)-2-(2-amino-5-chlorothiazol-4-yl)-2-(triphenylmethoxyimino]acetamido]-3-[1,3,4-thiadiazol-2-ylthio]-8-oxo-1-aza-bicyclo-[4.2.0]oct-2-ene-2-carboxylate diphenylmethyl ester (1.5 g) was added in portions. The reaction mixture was stirred at 0° C. for 3 hours, was allowed to warm up to room temp. and was evaporated to dryness. The residue was treated with diethyl ether (50 mL), and the solid that formed was filtered and dried to give the crude product. The crude product was purified on HP 20 initially with water elution until the pH was neutral, and thereafter with acetonitrile:water 80:20 to give the title compound (0.63 g.)

$^1$H NMR 400 MHz, (DMSO-$d_6$) δ 1.63–1.73 (m, 1H), 1.88–1.91 (m, 1H), 2.33–2.48 (m, 2H), 3.89–3.94 (m, 1H), 5.50 (dd, J=9 Hz, J=5 Hz, 1H), 7.28 (brs, 2H), 9.18 (d, J=9 Hz, 1H), 9.70 (d, J=9 Hz, 1H), 11.71 (s, 1H), 13.46 (brs, 1H).

EXAMPLE 7

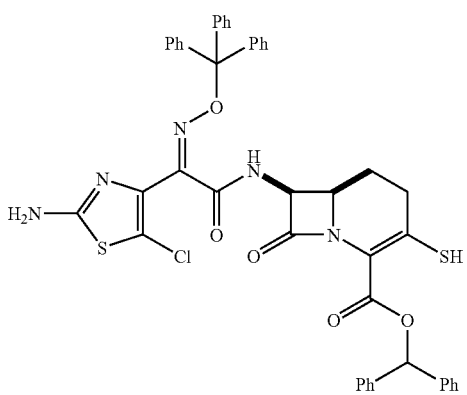

(7R)-7-[(Z)-2-(2-amino-5-chlorothiazol-4-yl)-2-(triphenylmethoxyimino]-acetamido]-3-mercapto-8-oxo-1-aza-bicyclo[4.2.0]oct-2-ene-2-carboxylate diphenylmethyl ester A solution of (7R)-7-[(Z)-2-(2-amino-5-chlorothiazol-4-yl)-2-(triphenylmethoxyimino]-acetamido]-3-chloro-8-oxo-1-aza-bicyclo[4.2.0]oct-2-ene-2-carboxylate diphenylmethyl ester (3.0 g, 0.0036 mol) in dimethylformamide (40 mL) was cooled to −20° C. and a solution of ammonium sulfide in water (20%, 5.7 mL) was added drop-wise. The mixture was stirred at −20° C. for 4 hours and then was poured into pH 3 phosphate buffer (100 mL). The resulting solid was filtered, washed with water and dried to afford the crude title compound (5.4 g).

$^1$H NMR 400 MHz, (DMSO-d$_6$) δ 1.64–1.82 (m, 2H), 2.24–2.32 (m, 2H), 3.87–3.92 (m, 1H), 5.73 (dd, J=9 Hz, J=5 Hz, 1H), 6.90 (s, 1H) 7.28–7.32 (m, 21H), 7.50 (d, J=7 Hz, 2H), 7.65 (d, j=7 Hz, 2H), 7.95 (s, 1H), 9.48 (d, J=9 Hz, 1H).

EXAMPLE 8

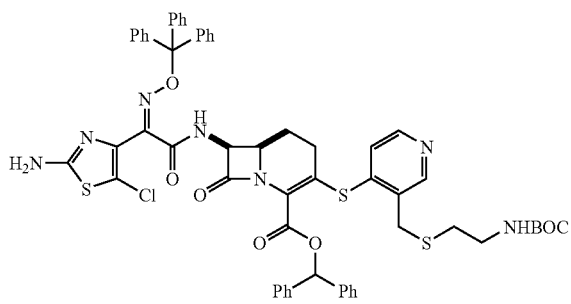

(7R)-7-[(Z)-2-(2-amino-5-chlorothiazol-4-yl)-2-(triphenylmethoxyimino]-acetamido]-3-[3-(N-tert-butoxycarbonylaminoethylthiomethyl)pyrid-4-ylthio]-8-oxo-1-aza-bicyclo[4.2.0]oct-2-ene-2-carboxylate diphenylmethyl ester To a solution of (7R)-7-[(Z)-2-(2-amino-5-chlorothiazol-4-yl)-2-(triphenylmethoxyimino]-acetamido]-3-mercapto-8-oxo-1-aza-bicyclo[4.2.0]oct-2-ene-2-carboxylate diphenylmethyl ester (3.0 g, 0.0036 mol) in dimethylformamide (30 mL) was added 3-(N-tert-butoxycarbonylaminoethylthiomethyl)-4-chloropyridine (1.3 g, 0.0043 mol) at room temperature. After stirring overnight, the reaction mixture was treated with water (200 mL), and the solid that formed was filtered and dried to afford the crude title compound (2.9 g).

$^1$H NMR 400 MHz, (DMSO-d$_6$) δ 1.38 (s, 9H), 1.60–1.82 (m, 2H), 2.27–2.35 (m, 2H), 2.43 (t, J=7 Hz, 2H), 3.11 (q, J=7 Hz, 2H), 3.75 (s, 2H), 3.98–4.00 (m, 1H), 5.77 (dd, J=9 Hz, J=5 Hz, 1H), 6.88 (s, 1H), 6.89 (d, J=7 Hz, 1H), 6.94 (q, J=7 Hz, 1H), 7.18 (d, J=7 Hz, 1H), 7.20–7.60 (m, 26H), 8.36 (d, J=5 Hz, 1H), 8.46 (s, 1H), 9.42 (d, J=9 Hz, 1H).

EXAMPLE 9

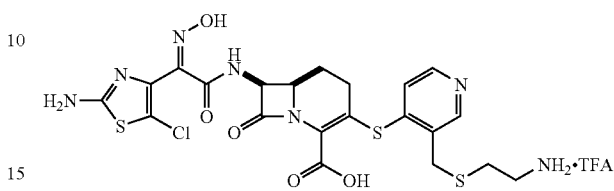

(7R)-7-[(Z)-2-(2-amino-5-chlorothiazol-4-yl)-2-(hydroxyimino]acetamido]-3-[3-(aminoethylthiomethyl)pyrid-4-ylthio]-8-oxo-1-aza-bicyclo[4.2.0]oct-2-ene-2-carboxylate, trifluoroacetic acid salt A solution of trifluoroacetic acid (10 mL), triethylsilane (5 mL) and dichloromethane (10 mL) was cooled to 0° C. and (7R)-7-[(Z)-2-(2-amino-5-chlorothiazol-4-yl)-2-(triphenylmethoxyimino]acetamido]-3-[3-(N-tert-butoxycarbonylaminoethylthiomethyl)-pyrid-4-ylthio]-8-oxo-1-aza-bicyclo[4.2.0]oct-2-ene-2-carboxylate diphenylmethyl ester (2.9 g, crude from previous step) was added in portions. The reaction mixture was stirred at 0° C. for 6 hours, was allowed to warm to room temp. and was evaporated to dryness. The residue was treated with diethyl ether (50 mL), and the solid that formed was filtered and dried to give 2.0 g of crude product. The crude product was purified on HP 20 initially with water elution until the pH was neutral, and thereafter with acetonitrile:water 80:20, to give the product (0.12 g).

$^1$H NMR 400 MHz, (DMSO-d$_6$) δ 1.75–1.90 (m, 2H), 2.23–2.34 (m, 2H), 2.65 (t, J=7 Hz, 2H), 3.04 (q, J=7 Hz, 2H), 3.87 (d, J=Hz, 2H), 3.95–4.00 (m, 1H), 5.53 (dd, J=9 Hz, J=5 Hz, 1H), 7.23 (d, J=6 Hz, 1H), 7.30 (brs, 2H), 7.80 (brs, 2H), 8.43 (d, J=5 Hz, 1H), 8.49 (s, 1H), 9.14 (d, J=9 Hz, 1H), 11.75 (s, 1H).

EXAMPLE 10

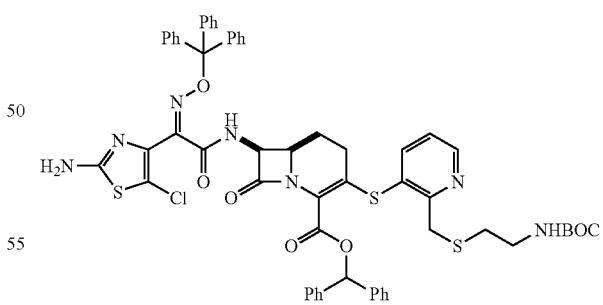

(7R)-7-[(Z)-2-(2-amino-5-chlorothiazol-4-yl)-2-(triphenylmethoxyimino]-acetamido]-3-[2-(N-tert-butoxycarbonylaminoethylthiomethyl)pyrid-3-ylthio]-8-oxo-1-aza-bicyclo[4.2.0]oct-2-ene-2-carboxylate diphenylmethyl ester To a solution of (2-{3-[2-(2-tert-butoxycarbonylaminoethyl-sulfanylmethyl)-pyridin-3-yldisulfanyl]-pyridin-2- ylmethylsulfanyl}ethyl)carbamic acid tert-butyl ester (1.3 g, 0.0022 mol) in acetonitrile (120 mL) was added sodium borohydride (0.12 g, 0.003 mol), and the mixture was stirred at room temp. for 18 hours. (7R)-7-[(Z)-2-(2-amino-5-chlorothiazol-4-yl)-2-(triphenylmethoxyimino]-acetamido]-3-chloro-8-oxo-1-aza-bicyclo[4.2.0]oct-2-ene-2-carboxylate diphenylmethyl ester (3.6 g, 0.0043 mol) was added in portions and the mixture was heated at reflux for 6 hours. The solvent was evaporated and the residue was partitioned between ethyl acetate (50 mL) and water (50 mL). The organic layer was separated, dried over anhydrous $MgSO_4$ and concentrated. The residue was treated with diethyl ether (50 mL), and the solid that formed was filtered and dried to give 3.6 g of crude product. The crude product was purified by column chromatography on silica gel (100 g), eluting with hexane: ethyl acetate 1:1, to give the title compound (1.15 g).

$^1$H NMR 400 MHz, (DMSO-$d_6$) δ 1.36 (s, 9H), 1.55–1.60 (m, 2H), 2.40–2.51 (m, 2H), 3.08 (q, J=7 Hz, 2H), 3.86–3.90 (m, 1H), 3.91 (s, 2H), 5.69 (dd, J=9 Hz, J=5 Hz, 1H), 6.90 (s, 2H), 7.20–7.60 (m, 28H), 7.85 (dd, J=Hz, J=2 Hz, 1H), 8.51 (dd, J=5 Hz, J=2 Hz, 1H), 9.44 (d, J=9 H).

EXAMPLE 11

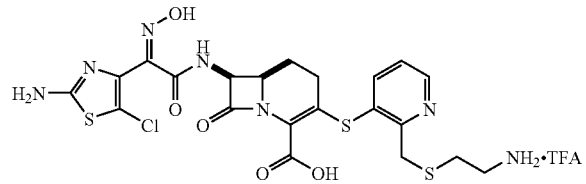

(7R)-7-[(Z)-2-(2-amino-5-chlorothiazol-4-yl)-2-(hydroxyimino]acetamido]-3-[2-(aminoethylthiomethyl)pyrid-3-ylthio]-8-oxo-1-aza-bicyclo[4.2.0]oct-2-ene-2-carboxylate, trifluoroacetic acid salt A solution of trifluoroacetic acid (5 mL), triethylsilane (3 mL) and dichloromethane (5 mL) was cooled to 0° C. and (7R)-7-[(Z)-2-(2-amino-5-chlorothiazol-4-yl)-2-(triphenylmethoxyimino]acetamido]-3-[2-(N-tert-butoxycarbonylaminoethylthiomethyl)-pyrid-3-ylthio]-8-oxo-1-aza-bicyclo[4.2.0]oct-2-ene-2-carboxylate diphenylmethyl ester (1.0 g, 0.9 mmol) was added in portions. The reaction mixture was stirred at 0° C. for 2 hours, was allowed to warm to room temp. and was evaporated to dryness. The residue was treated with diethyl ether (50 mL), and the solid that formed was filtered and dried to give 0.65 g of the title product.

$^1$H NMR 400 MHz, (DMSO-$d_6$) δ 1.56–1.66 (m, 1H), 1.78–1.86 (m, 1H), 2.08–2.18 (m, 2H), 2.73 (t, J=7 Hz, 2H), 3.03 (q, J=7 Hz, 2H), 3.81–3.86 (m, 1H), 4.01 (dd, J=17 Hz, J=14 Hz, 2H), 5.45 (dd, J=9 Hz, J=5 Hz, 1H), 7.37 (dd, J=8 Hz, J=5 Hz, 2H), 7.84 (brs, 2H), 7.86 (dd, J=8 Hz, J=2 Hz, 2H) 8.47 (dd, J=5 Hz, J=2 Hz, 1H), 9.12 (d, J=9 Hz, 1H), 11.70 (s, 1H).

Routes of Administration

Suitable routes of administration of a compound of this invention include, without limitation, oral, rectal, transmucosal, intramuscular, subcutaneous, intramedullary, intrathecal, direct intraventricular, intravenous, intravitreal, intraperitoneal, intranasal, aural or intraocular. The preferred routes of administration are oral and parenteral.

Alternatively, one might administer the compound in a local rather than systemic manner, for example, by preparation as a salve that is applied directly to the infected area or by injection of the compound directly into infected tissue. In either case, a sustained release formulation may be used.

The route of administration will dictate the composition/formulation of the compound used. The following is a brief, non-limiting discussion of pharmaceutical compositions that, under appropriate circumstances, may be useful with the compounds of this invention.

Pharmaceutical Compositions

A compound of the present invention or a physiologically acceptable salt thereof, can be administered as such to a patient or can be administered in pharmaceutical compositions comprising one or more suitable excipient(s). Techniques for formulation of drugs for use with various methods of administration can be found in *Remington's Pharmacological Sciences*, Mack Publishing Co., Easton, Pa., latest edition. The formulations and techniques discussed in Remington relate primarily to use with human patients; however, they may readily modified for use with non-human patients by techniques well-known to those skilled in the veterinary and agricultural arts.

Pharmaceutical compositions of the present invention may be manufactured by processes well known in the art, e.g., using a variety of well-known mixing, dissolving, granulating, dragee-making, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen.

For example, for injection, including, without limitation, intravenous, intramsclular and subcutaneous injection, the compounds of the invention may be formulated in aqueous solutions, preferably in physiologically compatible buffers such as Hanks' solution, Ringer's solution, physiological saline buffer or polar solvents including, without limitation, N-methyl-2-pyrrolidone, 2-pyrrolidone, other pyrrolidones, N,N-dimethylacetamide, N,N-dimethylformamide, dimethylsulfoxide, acetone and glycerol formal.

For transmucosal administration, penetrants appropriate to the barrier to be permeated may be used in the formulation. Such penetrants are generally known in the art.

For oral administration, the compounds can be formulated by combining the active compounds with pharmaceutically acceptable carriers well-known in the art. Such carriers enable the compounds of the invention to be formulated as tablets, pills, lozenges, dragees, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethylcellulose, sodium carboxymethylcellulose, and/or polyvinylpyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

For administration by inhalation, the compounds of the present invention can conveniently be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insulator may be formulated containing a powder mix of the compound and a suitable powder base such as lactose or starch.

The compounds may also be formulated for parenteral administration, including, without limitation, bolus injection or continuous infusion. Formulations for injection may be presented in unit dosage form, e.g., in ampoules or in multi-dose containers. Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, although often at the risk of greater toxicity.

Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few days to over 100 days. Depending on the chemical nature and the biological stability of the particular compound, additional stabilization strategies may be employed.

Pharmaceutical compositions useful herein also may comprise solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

A therapeutically effective amount of a compound of this invention can be used to treat a patient suffering from an antibiotic resistant bacterial infection such as that caused by MRSA, or other methicillin resistant strain, or a vancomycin-resistant or ampicillin-resistant strain. In particular, infections caused by resistant *S. aureus* may be treated with a compound of this invention. Exemplary *S. aureus* strains that may be treated include, without limitation, *S. aureus* Col (Meth$^R$)(bla−), *S. aureus* 76 (Meth$^R$)(bla+), *S. Aureus* ATCC 29213, *S. Aureus* ATCC 25913, *S. Aureus* ATCC 32432 and *S. Aureus* Col8A.

In addition, *Enterococcus* strains such as, without limitation, *E. fæcium* ATCC 35667 and *E. fæcalis* ATCC 29212 may be effectively treated.

The compositions containing a compound or compounds of this invention can be administered for prophylactic or therapeutic treatment. In therapeutic applications, the compound(s) is administered to a patient already suffering from an infection, as described above, in an amount sufficient to cure or at least partially arrest the symptoms of the infection. The required dose is referred to as a therapeutically effective amount or dose. The dose will depend on the severity and course of the infection, previous therapy, the patient's health status and response to the drugs, and the judgment of the treating physician.

For prophylactic applications, the compounds of the invention are administered to a patient who is not yet infected but who is particularly at risk of infection such as, for example, a transplant patient who is being given immuno-suppressants to prevent rejection. The dose used is referred to as a prophylactically effective amount or dose. In this use, the precise amounts again depend on the patient's state of health, weight, and the like. And, as noted previously, a prophylactic amount can also be administered to maintain the level of improvement in a patient's health and well-being effected by previous therapeutic dose(s).

Once the condition of a patient who has received a therapeutic dose has improved, a maintenance dose, similar to a prophylactic dose, may be administered, if necessary. The dosage or frequency of administration, or both, can be reduced as a function of the symptoms, to a level at which the improved condition is maintained. Patients may require intermittent treatment on a long-term basis assure control of the infection.

Dosage

The proper dosage to achieve a therapeutically or prophylactically effective amount will depend on the severity and course of the infection, previous therapy, the patient's general health status, his or her response to the drugs, etc., all of which are within the knowledge, expertise and judgment of the treating physician.

In general, a suitable effective dose of the compound of the invention will be in the range of 0.1 to 10,000 milligram (mg) per recipient per day, preferably in the range of 20 to 2000 mg per day. The desired dosage is preferably presented in one, two, three, four or more sub-doses administered at appropriate intervals throughout the day. These sub-doses can be administered as a unit dosage, for example, a single dose of 5 to 1000 mg, preferably 10 to 100 mg of active ingredient. Preferably, the compounds of the invention will be administered in amounts of between about 2.0 mg/kg to 250 mg/kg of patient body weight, between about one to four times per day.

Once improvement of the patient's condition is observed, a maintenance or prophylactic dose may be administered if desired by the treating physician. The dosage, frequency, or both, can be reduced as a function of the patient's response to a level at which the improvement persists. When the symptoms have been alleviated to the desired level, treatment may be ceased although some patients may require intermittent treatment on a long-term basis should flare-ups of the symptoms recur.

Biological Evaluation

It will be appreciated that, in any given series of compounds, a spectrum of biological activity will be observed. In its most preferred embodiment, a compound of this invention will demonstrate activity superior to vancomyin or cefotaxime against bacterial infections resistant to conventional β-lactam antibiotics such as methicillin and ampicillin. The following procedures may, without limitation, be used to evaluate the compounds of this invention.

The in vitro MIC for bacterial isolates may be obtained in the following manner: a test compound is incorporated into a series of two-fold dilutions in liquified Mueller-hinton agar. Upon solidification, a number of different bacterial strains are spot-inoculated onto the surface of the agar. The agar is incubated overnight and the MIC breakpoint determined by observing the lowest drug concentration that completely inhibits growth. The procedures used in these experiments are generally those standardized by the National Committee for Clinical Laboratory Standards (NCCLS), as set forth in the NCCLS publication entitled "Methods for Dilution Antimicrobial Susceptibility Tests (1991), which is incorporated by reference as if fully set forth herein. The following exemplified such a procedure although it is to be understood that modifications of the procedure may be implemented as required.

Aliquots of the test compounds are prepared in phosphate buffered saline (PBS) at pH approximately 7.2. Tween 20 or dimethylsulfoxide (DMSO) are added if necessary to solubilize the compound and vortexing, sonicating and gentle heating may also be employed. Typically, the concentration of the stock solution is 10× that of the highest compound concentration to be used. Serial two-fold dilutions are prepared down to the lowest concentration to be tested. Each compound concentration is tested in duplicate. A control plate using a reference drug such as cefotaxime, vancomycin or imipenem is used as a postive control. A negative control plate containing no drug or compound is also prepared.

A few isolated colonies are retrieved from a pure culture prepared on agar plates and transferred to a tube of nutrient broth and allowed to grow at 35–36° C. until log-phase growth is achieved, usually about 4–6 hours. The broth is then added dropwise to PBS until the turbidity of the suspension matches a 0.5 McFarland standard which is equal to approximately $10^8$ cfu/ml.

The test plates containing the compound dilutions and the control plates are then inoculated with the PBS suspension. The plates are then incubated for 16–20 hours at 35–36° C. The plates are then observed to determine which concentration of the test compound is the MIC.

Compounds that show superior activity in in vitro tests can then be further evaluated in animal models such as rats and mice. The following is an example of such a test, it being understood that the example is not to be construed as limiting the scope of this invention in any manner whatsoever.

*Staphylococcus aureus* strain Smith (ATCC 13709, penicillin-susceptible) or strain 76 (methicillin-resistant) is grown overnight at 37° C. in brain-heart infusion broth (BHIB). The following morning, it is sub-cultured to fresh BHIB and incubated for 4–5 h at 37° C. The cells are harvested by centrifugation, washed twice with PBS, and adjusted to the desired inoculum. The cell suspension is then mixed with an equal volume of sterile 14% hog-gastric mucin (Comber K. R.; Osborne C. D.; Sutherland R., "Comparative effects of amoxicillin and ampicillin in the treatment of experimental mouse infections," *Antimicrobial Agents and Chemotherapy*, 1995, 7(2):179–185). The inoculum is kept in an ice bath until ready for use (preferable less than one hour).

Male Swiss-Webster mice are challenged intraperitoneally with 0.5 mL of the above bacterial suspension of *S. aureus* strain Smith ($LD_{50}$). Test compounds are administered subcutaneously in 0.1 mL volumes immediately after inoculation and again 2 hours later. The animals are then observed for 72 h. The total dose associated with 50% survival ($ED_{50}$) is then determined using the probit method (Pasiello, A. P., J. M. Essigmann, and G. N. Wogan, "Rapid and accurate determination of median lethal dose (LD50) and its error with a small computer," J. Toxicol. Environ. Health, 1977, 3:797–809).

As noted previously, to be an effective anti-MRSA compound, a carbacephem must exhibit a proper balance of potency versus serum protein binding. The following procedure may be used to evaluate serum binding: compounds are incubated in serum for 10 min at 37° C. in a shaking water bath. Then a serum ultrafiltrate is obtained by centrifugation of ultra-filtration units (Amicon Centrifree) for, say, 20 minutes at 25° C. Compound content in the ultrafiltrate is quantified by HPLC using standards prepared in blank ultra-filtrate undergoing similar processing.

Representative compounds of this invention were tested against two isolates of MRSA, MRSA COL and MRSA 76, against which current clinical β-lactam antibiotics are ineffective, as they exhibit MICs≧16 μg/mL. In addition, the human serum binding vales of the compounds were determined, and the results are shown in Table 1. As can be seen, the compounds all exhibit MICs of 2 μg/mL or less and serum binding of 89.4% or less, numbers which indicate that these compounds should be highly effective for treating infections caused by these strains. It is expected that the compounds will be equally, if not more, potent against other resistant strains of bacteria as well as bacteria which are susceptible to current clinical antibiotics. The range of utility of the compounds herein can easily be established by those skilled in the art using the disclosures herein and all bacteria within the useful range are within the scope of this invention.

TABLE 1

| Compound Structure | MIC (μg/mL) | | Human Serum Binding |
| --- | --- | --- | --- |
| | MRSA COL | MRSA 76 | |
| (structure) | 2 | 2 | 66.9% |
| (structure) | 1 | 2 | 68.0% |
| (structure) | 1 | 1 | 74.5% |
| (structure) | 1 | 2 | 89.4% |

CONCLUSION

While the above description describes particular embodiments and examples illustrating the invention, those skilled in the art will recognize that the invention may be practiced in a variety of alternative ways, for example, the compounds herein may be synthesized by many different routes. All such variations are within the scope of this invention.

Other embodiments of this invention are contained in the following claims.

What is claimed is:

1. A compound having the chemical structure:

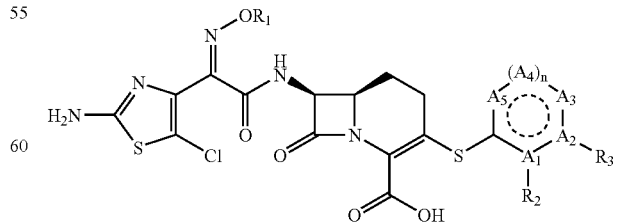

or a salt thereof, wherein:
n is 0 or 1, wherein:
when n is 0:

R₁ is hydrogen;
A₁ is selected from the group consisting of oxygen and sulfur;
R₂ does not exist;
A₂ is carbon;
A₃ and A₅ are independently selected from the group consisting of carbon and nitrogen such that the resulting ring is aromatic; and,
R₃ is selected from the group consisting of hydrogen, —NH₂ and —CH₂S(CH₂)₂NH₂;
when n is 1:
A₁ is carbon;
one or two of A₂, A₃, A₄ and A₅ is/are nitrogen, the rest are carbon;
R₂ is —CH₂S(CH₂)₂NH₂;
if A₂ is carbon, R₃ is hydrogen; if A₂ is nitrogen, R₃ does not exist; and,
R₁ is selected from the group consisting of:
hydrogen;
—CH₃;
—CH₂CH₃;
—CH₂F; and,
—CH₂CH₂F.

2. The compound or salt of claim 1, wherein:
n is 0;
A₁ is sulfur;
A₃ and A₅ are nitrogen; and,
R₃ is hydrogen.

3. The compound or salt of claim 1, wherein:
n is 0;
A₁ is sulfur;
A₃ and A₅ are nitrogenn; and,
R₃ is —NH₂.

4. The compound or salt of claim 1, wherein:
n is 1; and
one of A₂, A₃, A₄ and A₅ is nitrogen, the others being carbon.

5. The compound or salt of claim 4, wherein A₂ is nitrogen.

6. The compound or salt of claim 4, wherein A₃ is nitrogen.

7. The compound or salt of claim 1, having the chemical structure:

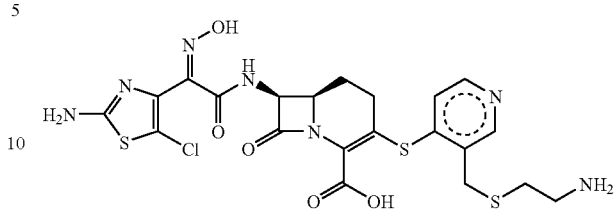

8. The compound or salt of claim 1, having the chemical structure:

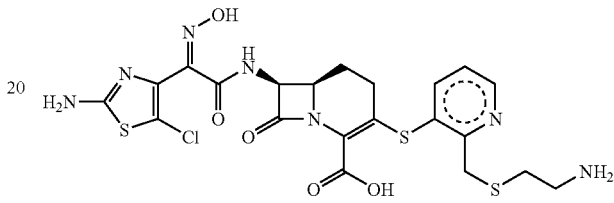

9. A method of treating or preventing a bacterial infection comprising administering a pharmaceutically effective amount of a compound or salt of claim 1 to a patient in need thereof.

10. The method of claim 9, wherein the bacterial infection is caused by a β-lactam antibiotic-resistant bacterium.

11. The method of claim 10, wherein the β-lactam antibiotic-resistant bacterium is a methicillin-resistant *Staphylococcus* bacterium.

12. A pharmaceutical composition, comprising:
a compound or salt of claim 1; and,
one or more pharmaceutically acceptable excipients.

* * * * *